United States Patent
Winn et al.

(10) Patent No.: US 10,740,500 B1
(45) Date of Patent: Aug. 11, 2020

(54) META DATA MANAGEMENT SYSTEM FOR A MULTI-USER CAX ENVIRONMENT

(71) Applicant: United Technologies Corporation, Hartford, CT (US)

(72) Inventors: Joshua Daniel Winn, Ellington, CT (US); William A. Sowa, Simsbury, CT (US)

(73) Assignee: Raytheon Technologies Corporation, Farmington, CT (US)

( * ) Notice: Subject to any disclaimer, the term of this patent is extended or adjusted under 35 U.S.C. 154(b) by 1141 days.

(21) Appl. No.: 14/825,496

(22) Filed: Aug. 13, 2015

(51) Int. Cl.
| A61B 5/04 | (2006.01) |
| G06F 17/50 | (2006.01) |
| G06F 30/00 | (2020.01) |
| H04L 29/08 | (2006.01) |
| A61B 5/00 | (2006.01) |

(52) U.S. Cl.
CPC ............. *G06F 30/00* (2020.01); *A61B 5/72* (2013.01); *H04L 67/10* (2013.01)

(58) Field of Classification Search
CPC ... H04L 65/403; G06Q 10/00; G06F 17/5004; G06F 19/322; G06F 17/30165; G06T 19/003; G06K 9/00369
See application file for complete search history.

(56) References Cited

U.S. PATENT DOCUMENTS

| 5,920,725 | A * | 7/1999 | Ma ........................ G06F 8/656 717/171 |
| 6,295,513 | B1 * | 9/2001 | Thackston ......... G05B 19/4099 703/1 |
| 7,340,383 | B2 * | 3/2008 | Mayuzumi ............ G06Q 40/08 345/418 |
| 7,813,822 | B1 * | 10/2010 | Hoffberg ............ G06K 9/00369 381/73.1 |
| 8,229,715 | B1 | 7/2012 | Teller et al. |
| 9,292,261 | B1 * | 3/2016 | Bouldin .................. G06Q 10/00 |
| 2003/0103089 | A1 * | 6/2003 | Ramani .................... G06F 17/50 715/848 |
| 2007/0174281 | A1 * | 7/2007 | Chase ................. H04N 7/17318 |

(Continued)

OTHER PUBLICATIONS

Xu, Yue, A Flexible Context Architecture for a Multi-User GUI, Thesis, Dec. 2010, Department of Mechanical Engineering, Brigham Young University.

(Continued)

*Primary Examiner* — Kandasamy Thangavelu
(74) *Attorney, Agent, or Firm* — Carlson, Gaskey & Olds, P.C.

(57) ABSTRACT

A software agnostic multi-user CAx environment system includes a host computer with a processor and a memory. The processor and memory are configured to operate a multi-user CAx environment. The host computer is configured to communicate with a plurality of local computers. Each of the local computers includes at least one CAx software package and is configured to operate a local CAx environment of the multi-user CAx environment. A part database is configured to store multiple part files. Each of the part files includes at least one component having multiple features. At least one meta data file is stored within the part database. The meta data file is linked to at least one of the plurality of features.

15 Claims, 5 Drawing Sheets

(56) References Cited

U.S. PATENT DOCUMENTS

| | | | |
|---|---|---|---|
| 2010/0217566 A1* | 8/2010 | Wayne | G06F 17/5004 703/1 |
| 2013/0110892 A1* | 5/2013 | Wood | G06F 17/30165 707/827 |
| 2013/0144566 A1 | 6/2013 | De Biswas | |
| 2013/0159021 A1* | 6/2013 | Felsher | G06F 19/322 705/3 |
| 2014/0095122 A1* | 4/2014 | Appleman | G06T 19/003 703/1 |
| 2014/0149882 A1 | 5/2014 | Nysetvold et al. | |
| 2014/0195963 A1* | 7/2014 | Cheung | G06F 17/50 715/781 |
| 2014/0222387 A1 | 8/2014 | Cannon et al. | |
| 2014/0222919 A1 | 8/2014 | Nysetvold et al. | |
| 2014/0236550 A1 | 8/2014 | Nysetvold et al. | |
| 2014/0244588 A1* | 8/2014 | Awe | G06F 11/1446 707/649 |
| 2014/0278275 A1* | 9/2014 | Han | G06F 17/5004 703/1 |
| 2014/0317531 A1* | 10/2014 | Bowman, Jr. | H04L 65/403 715/751 |
| 2014/0358997 A1* | 12/2014 | Boulkenafed | H04L 12/18 709/203 |
| 2015/0112647 A1* | 4/2015 | Currin | G06Q 50/06 703/1 |

OTHER PUBLICATIONS

Red, Edward, David French, Ammon Hepworth, Greg Jensen, and Brett Stone, Multi-User Computer-Aided Design and Engineering Software Applications, Cloud-Based Design and Manufacturing (CBDM), Jan. 1, 2014, pp. 25-62, Springer International Publishing.

Red, Edward, Greg Jensen, Jordan Ryskamp, and Kenneth Mix, NXConnect: Multi-User CAx on a Commercial Engineering Software Application, Department of Mechanical Engineering, Brigham Young University. 2010 PACE Global Annual Forum.

* cited by examiner

META DATA MANAGEMENT SYSTEM FOR A MULTI-USER CAX ENVIRONMENT

BACKGROUND

This disclosure relates to computer-aided technologies (CAx), and more particularly, to visualization of component designs in a computing environment.

CAx software is used to develop tools, parts, assemblies, structures and other components using a computer system during the design, analysis, and manufacturing phases, for example. CAx software may be used by a user or group of users to build, analyze, and manufacture complex elements. CAx software is typically restricted to a single user paradigm, wherein only a single user can edit a model or part file within a CAx software application at a time. The user must exit the file before another user is allowed to access it.

SUMMARY

In one exemplary embodiment a system for executing software agnostic multi-user CAx environments includes a host computer including a processor and a memory, the processor and memory being configured to operate a multi-user CAx environment, the host computer configured to communicate with a plurality of local computers, each of the local computers including at least one CAx software package and being configured to operate a local CAx environment of the multi-user CAx environment, a part database configured to store a plurality of part files, each of the part files including at least one component having a plurality of features, and at least one meta data file stored within the part database, the meta data file being linked to at least one of the plurality of features.

In another exemplary embodiment of the above described system, the at least one meta data file stored within the part database is linked to the at least one of the plurality of features via a direct link.

In another exemplary embodiment of any of the above described systems, the at least two of the plurality of features of the at least one component are linked to the same meta data file within the part file.

In another exemplary embodiment of any of the above described systems, the at least one meta data file stored within the part database is linked to the at least one of the plurality of features via a meta data index file.

In another exemplary embodiment of any of the above described systems each of the meta data index files is stored within a corresponding part file, and links to a corresponding meta data file stored within a meta data file database in the part database.

In another exemplary embodiment of any of the above described systems the meta data file database is a distinct database from the part database.

In another exemplary embodiment of any of the above described systems at least two of the plurality of features of the at least one component are linked to the same meta data file via distinct meta data index files.

In another exemplary embodiment of any of the above described systems each unique meta data file is stored a single time within a meta data file database in the part file database.

In another exemplary embodiment of any of the above described systems the multi-user CAx environment includes a meta data module configured to display one of an icon and a string characters in association with a feature, when the feature is displayed in the multi-user CAx environment.

In another exemplary embodiment of any of the above described systems the multi-user CAx environment further includes a meta data notification module configured to notify a user of a presence of meta data files associated with a feature of a component displayed in the multi-user CAx environment.

In another exemplary embodiment of any of the above described systems the at least one meta data file is at least one file having a file type outside of file types associated with the multi-user CAx system.

In another exemplary embodiment of any of the above described systems the at least one meta data file is a file containing information related to a feature of a component to which the at least one meta data file is assigned, and wherein the information related to the feature is information that is outside the scope of the multi-user CAx system.

An exemplary method for facilitating multi-user design in a CAx system includes hosting a multi-user CAx environment at a host computer including a processor and a memory, the host computer communicating with a plurality of local computers, each of the local computers operating one of a plurality of local CAx environments within the multi-user CAx environment, retrieving at least one part file having a plurality of features from a part database, the part database being configured to store multiple part files, and displaying a meta data notification in each of the local CAx environments accessing a feature of the at least one part file, the feature being associated with a meta data file in the part database.

A further example of the above described exemplary method includes displaying a meta data notification comprises displaying an icon at or near the feature in one of a three dimensional and a sketch view.

A further example of any of the above described exemplary methods includes displaying a meta data notification comprises displaying a string of characters in an attribute information view of a non-geometric feature.

A further example of the above described exemplary method further includes opening the meta data file in one of the local CAx environments in response to a user in the local CAx environment interacting with the notification.

An exemplary method for organizing a part database for a multi-user CAx system includes storing a plurality of part files within a part database of a multi-user CAx system, wherein the multi-user CAx system includes a host computer including a processor and a memory, the processor and memory being configured to operate a multi-user CAx environment, and the host computer is configured to communicate with a plurality of local computers, each of the local computers including at least one CAx software package and being configured to operate a local CAx environment of the multi-user CAx environment, storing at least one meta data file within the part database, and associating the at least one meta data file in the part database with at least one feature of a corresponding part file in the plurality of part files.

In a further example of the above described exemplary method the association between the at least one meta data file and the at least one feature is a direct link.

In a further example of any of the above described exemplary methods the association between the at least one meta data file and the at least one feature is via an index file associated with the at least one feature.

In a further example of any of the above described exemplary methods multiple features of the corresponding part file are associated with a single meta data file, and wherein each meta data file is stored exactly one time in the part database.

The various features and advantages of this disclosure will become apparent to those skilled in the art from the following detailed description. The drawings that accompany the detailed description can be briefly described as follows.

BRIEF DESCRIPTION OF THE DRAWINGS

The various features and advantages of the disclosed embodiments will become apparent to those skilled in the art from the following detailed description. The drawings that accompany the detailed description can be briefly described as follows.

DETAILED DESCRIPTION

Figure 1:
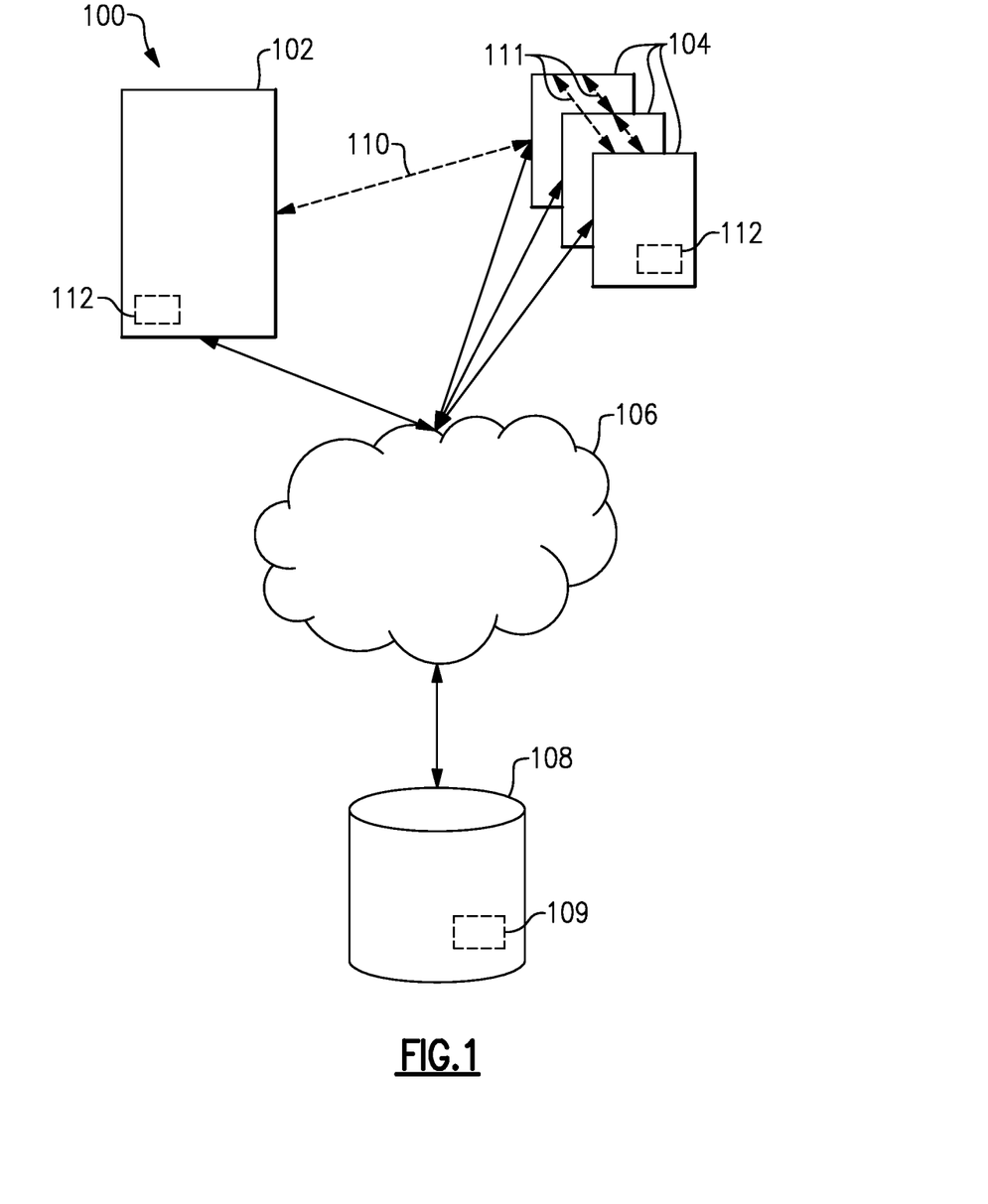
FIG. 1 illustrates a system for a multi-user CAx environment, according to an embodiment.

FIG. 1 illustrates an embodiment computing architecture or system 100 for executing a multi-user CAx environment, according to an embodiment. The system 100 includes a host computer 102. The host computer 102 may include one or more of a computer processor, memory, storage means, network device, and input and/or output devices and/or interfaces. The host computer 102 is configured to execute one or more software programs. In one embodiment, the host computer 102 is more than one computer jointly configured to process software instructions serially or in parallel.

In some embodiments, the host computer 102 is in communication with one or more networks such as a network 106 comprised of one or more computing devices. The system 100 additionally includes one or more client computers 104. The host computer 102 and the one or more client computers 104 typically include one or more of a computer processor, memory, storage means, network device and input and/or output devices and/or interfaces according to some embodiments. The memory may, for example, include UVPROM, EEPROM, FLASH, RAM, ROM, DVD, CD, a hard drive, or other computer readable medium which may store data and/or the CAx software of this description. The host computer 102 and the one or more client computers 104 may be a desktop computer, laptop computer, smart phone, tablet, or any other computer device. In some embodiments, one or more of the host computer 102 and the one or more client computers 104 include an input device, such as a keyboard and mouse, and one or more output devices such as a monitor, speakers, printers, etc. The interface facilitates communication with the other systems and/or components of the network 106.

In some embodiments of collaboration between multiple CAx users, each of the client computers 104 is a user workstation capable of accessing and locally running CAx software and providing a CAx environment 112. In some embodiments, the CAx environment 112 is operable to perform one or more CAx functions including at least one CAx tool, including a computer-aided design (CAD), computer-aided engineering (CAE) and/or computer-aided manufacturing (CAM) tool, for example. In other embodiments, at least one of the client computers 104 is operable to execute different CAx functions. In some embodiments, the CAx environment 112 provides a display or visualization of a component design stored one or more part files, according to one or more visualization settings, and can be provided via one or more graphical user interfaces (GUI).

In some embodiments, the one or more client computers 104 are configured to communicate with the host computer 102 directly via a direct client interface 110 or over the network 106. The one or more client computers 104 are configured to execute one or more software programs, such as a CAx package. In some embodiments, the CAx package is configured to communicate with the host computer 102 either over the network 106 or directly through the direct client interface 110. In another embodiment, the one or more client computers 104 are configured to communicate with each other directly via a peer-to-peer interface 111.

The network 106 may be a private local area network (LAN), a private wide area network (WAN), the Internet, a mesh network, or any other network as is known in the art. The system 100 additionally includes at least one storage system 108, which in some embodiments is operable to store or otherwise provide data to other computing devices. In one embodiment, the storage system 108 is a storage area network device (SAN) configured to communicate with the host computer 102 and/or the one or more client computers 104 over the network 106. In another embodiment, the storage system 108 is located within the host computer 102 or within at least one of the client computers 104. The storage system 108 may be configured to store one or more of computer software instructions, data, CAx files, database files, configuration information, etc.

In some embodiments, the system 100 is a client-server architecture configured to execute computer software on the host computer 102, which is accessible by the one or more client computers 104 using either a thin client application or a web browser executing on the one or more client computers 104. In some embodiments, the host computer 102 loads the computer software instructions from local storage, or from the storage system 108, into memory and executes the computer software using the one or more computer processors.

In some embodiments of the multi-user CAx architecture, each part file is stored within a database 109 at a central location, for instance at storage system 108. In another embodiment, the database 109 is stored at host computer 102 or is a distributed database provided by one or more of the client computers 104. In some embodiments, the database 109 is a relational database, and each part file in the database 109 is associated with a sub-assembly or assembly. In some embodiments, the database 109 is linked or otherwise corresponds to multiple part files. In an embodiment, the database 109 is configured to store data corresponding the component design one or more database records or entries, rather than linking or otherwise associating one or more part files to the database 109.

Each part file comprises one or more features, each feature corresponding to one or more feature types discussed below. In some embodiments, the part file includes a part tree or another data structure to organize and associate the features in a parent-child relationship between different features and/or part files. Each feature can be applied to one or more base features which together comprise the component design. Although the teachings of this disclosure refer primarily to featured-based CAx tools or systems, it should be appreciated that other CAx tools, systems or environments can benefit from the teachings herein, including geometrical-based CAD models.

The term "feature type" is defined as a geometric or non-geometric operation, or a result of such operation, available in a CAx tool to characterize a component design. The various feature types can be stored in one or more software libraries as one or more data classes which can be instantiated by the CAx tool.

The term "feature" refers to an instance of a feature type, which can include one or more software commands, or a result of its operation (such as a geometric object). Each feature is represented by a data set and has one or more parameters or attributes, such as a unique feature identifier, a feature type, a relative or absolute spatial position or orientation, body type such as a wireframe or solid, and/or its hierarchical relation to other features in a part tree, for example.

Some geometric feature types include two-dimensional sketches comprised of one or more one-dimensional geometries, such as points, lines or curves, and two-dimensional geometries such as rectangles or ellipses. A sketch, in some instances, provides a rough approximation of the desired dimensioning of the various aspects of a component design. In yet other embodiments, the feature types include various operations to create or modify solid(s) or other three-dimensional geometry such as wireframes, from one or two dimensional features. These various feature types include extrude(s), revolve(s), loft(s), sweep(s), chamfer(s), boundaries, and meshes, for example. The feature types can include operations such as a Boolean operation to add or subtract one feature from another feature, a mirror or a pattern operation to replicate at least one other feature, and an edge blend operation.

Various non-geometric feature types are contemplated including datum such as point(s), plane(s), axes, and coordinate system(s) utilized to arrange or orient other features, and in some instances may not comprise a final design of the component. Other non-geometric feature types can be used to further characterize a base feature comprising a component design, such as surface shading and coloring, material composition and dimensions. Of course, many other feature types utilized to create and further define the various aspects of a component design are contemplated within the teachings of this disclosure.

These various feature types and corresponding features typically have different levels of relevance to various disciplines involved in the collaboration of a component design. Each feature type and feature can also have different levels of applicability with respect to artifacts of the design process, including two-dimensional drawings such as schematics, engineering drawings or blueprints, wireframe models, surface models, and solid models, and also as inputs to other CAx tools such as finite element analysis (FEA) and computational fluid dynamics (CFD) models.

In some embodiments, the CAx environment 112 is configured to designate one or more features or feature types as a layer. Example layers include sketches, wireframes and solids, which in some embodiments are provided by the CAx software as default layer(s). In other embodiments, a user manually selects feature(s) and/or feature type(s) to be associated with at least one custom layer. In some embodiments, each layer is defined at system initialization, and in other embodiments, each layer is defined during operation. Each layer is utilized to filter the selected features or feature types in a part file loaded into the CAx environment.

Multiple users each provided with a CAx environment 112 via the client computers 104 are able to simultaneously access each part file stored in the database 109 and are able to make modifications to various aspects of a component design corresponding to one or more part files. In some embodiments, the part file is stored locally at the storage system 108, with local copies of the part file at the client computers 104 being synchronized periodically. Modifications to each part file are communicated to each CAx environment currently accessing the part file, either in real-time or periodically utilizing a synchronization scheme. Display or visualization of the modification is therefore made substantially immediately available in CAx environments accessing the same part file, which can assist the multiple users in identifying conflicts or inconsistencies in various aspects of a component design, thereby ensuring that a particular design intent is met.

In some situations, the multiple users who use a CAx environment 112 are assigned with different level(s) of access to the component design via a user profile. For example, the component design, or various aspects of the component design including the feature(s) or feature type(s), can be associated with one or more of the level(s) of access. In some embodiments, different levels of access are designated for users that are restricted from access due to export controls, security classification or proprietary restrictions. Other restricted and unrestricted levels of access are contemplated in this disclosure, including job disciplines and organization structures, for example. Accordingly, it may be desirable to limit the visualization of a particular aspect of a component design depending on the level(s) of access provided to a particular user profile. Each user profile corresponds to one or more access lists setting the level(s) of access for each user profile.

Figure 2A:
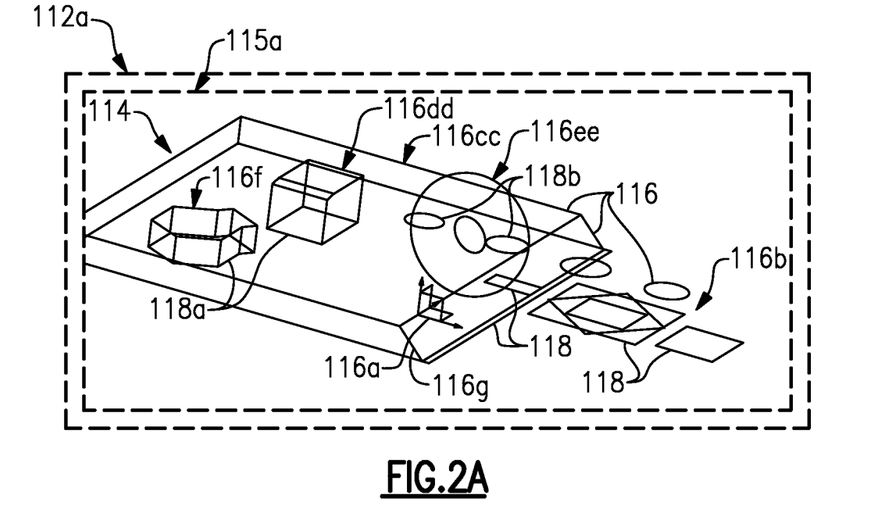
FIG. 2A illustrates a sample component design displayed in a first CAx environment, according to an embodiment.
Figure 2B:
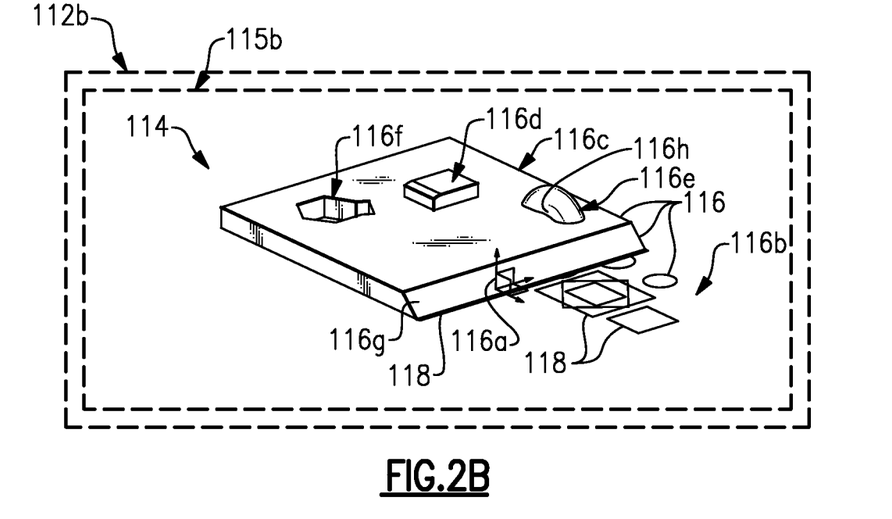
FIG. 2B illustrates the sample component design of FIG. 2A displayed in a second CAx environment, according to an embodiment.

FIGS. 2A-2B illustrate one embodiment in which two users collaborate on various aspects of a component design 114. In this embodiment, a first user is provided with a first CAx environment 112a, and a second user is provided with a second CAx environment 112b, shown in FIGS. 2A-2B respectively. Each of the CAx environments 112a, 112b is associated with a different one of the client computers 104, for example.

The example component design 114 includes one or more features 116 each corresponding to a feature type. The features 116 shown in FIG. 2A include a datum coordinate system 116a, and a sketch 116b having one or more sketch entities or geometries 118, 118a, 118b illustrated as ellipses and rectangles, for example. Some features 116 shown in FIG. 2B include solids such as extrudes 116c, 116d, which are applied to geometries 118, 118a, 118b of the sketch 116b and are characterized by wireframes 116cc, 116dd shown in FIG. 2A. Other example features include a hole or Boolean 116f forming an opening in the extrude 116c, and a chamfer 116g applied to extrude 116c. Non-geometric features include surface shading 116h (shown in FIG. 2B) applied to the rotate 116e feature.

Each of the multiple users is able to select one or more visualization settings to characterize the display of the component design 114 in a viewing frustum 115a, 115b provided by a CAx environment 112 based on the particular situation, as illustrated in FIGS. 2A-2B. For the purposes of this disclosure, the term "visualization setting" means data corresponding to one or more features, feature types, layers or other parameters which can be utilized to display a component design 114 in a CAx environment 112. The term "viewing frustum" refers to a region of modeling space in a window of the CAx environment 112 modeling the component design 114 that characterizes the display of a model or component design 114, in a graphical user interface (GUI) for example. The viewing frustum is characterized by the spatial position and/or orientation of the component design 114 in the modeling space. The CAx environment 112 displays selected portions of the component design 114 stored in one or more part files based on these visualization setting(s). Accordingly, modifications or updates made by other user(s) to the component design may not be displayed in the CAx environment 112.

FIGS. 2A and 2B illustrate different visualization settings for CAx environments 112a, 112b. As illustrated by the CAx environment 112a in FIG. 2A, the user has selected one or more visualization settings to show the wireframe geometries 116cc, 116dd, 116ee and to hide the corresponding solid features 116c, 116d, 116e. In the CAx environment 112b shown in FIG. 2B, the user has selected one or more visualization settings to show solid features 116c, 116d, 116e and to hide wireframes 116c, 116d, 116f, for example. The visualization settings of each CAx environment 112 can be customized according to the needs of a particular situation even though each of the users is working on the same component design 114.

In some examples, a part file stored within the database 109 in the storage system 108, will include one or more components. In such an example, each of the components can be worked on individually, and are interfaced together to form the completed part file. Certain part files can include meta information regarding how the components are interfaced with each other. Meta information includes any non-CAx format information regarding a given part file, feature interface, or other aspect of a component within the CAx database. By way of example, the meta interface can be a specification sheet saved in a document or text format, a slide show format, a .pdf format, or any other computer information format.

The meta information is associated with, or connected to, one or more features within the part file containing the meta information. When the associated feature(s) are geometric in nature, an icon is presented on the corresponding geometric feature in a display view indicating that there is meta data associated with that specific feature. Alternatively, when the associated feature is non-geometric in nature, a specific string of characters is stored within the attribute information for the non-geometric feature. The specific string of characters identifies that there is corresponding meta data and provides a link to the meta data file.

With continued reference to FIGS. 1, 2A and 2B, FIGS. 3A and 3B illustrate views of multiple components 214a, 214b within a single part file. Each of the components 214a, 214b is being simultaneously viewed in a viewing frustum 215a, 215b in separate CAx environments 212a, 212b by distinct users. Each of the components 214a, 214b includes multiple features and surfaces that are displayed in a three dimensional view. Further, the components 214a, 214b are designed to interface with each other within the part file containing both the components 214a, 214b.

Figure 3A:
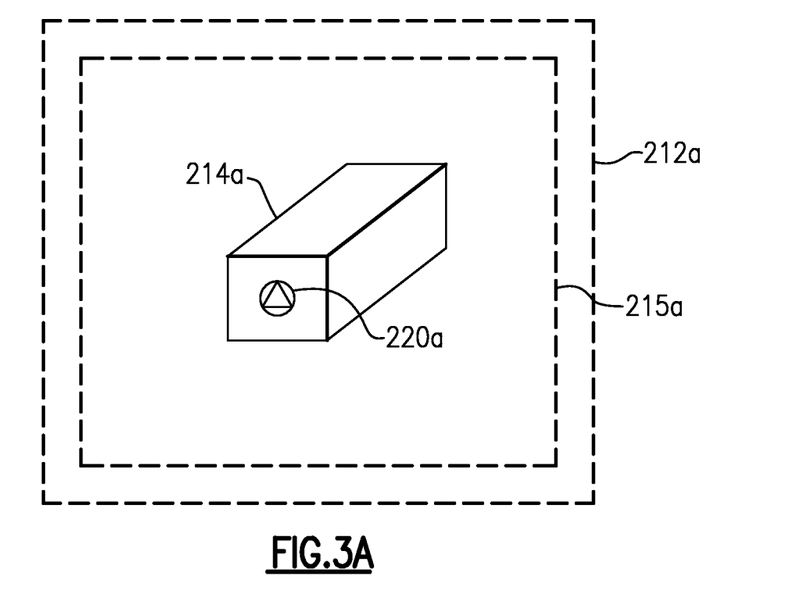
FIG. 3A illustrates a sample component of a part file displayed in a first CAx environment, according to an embodiment.
Figure 3B:
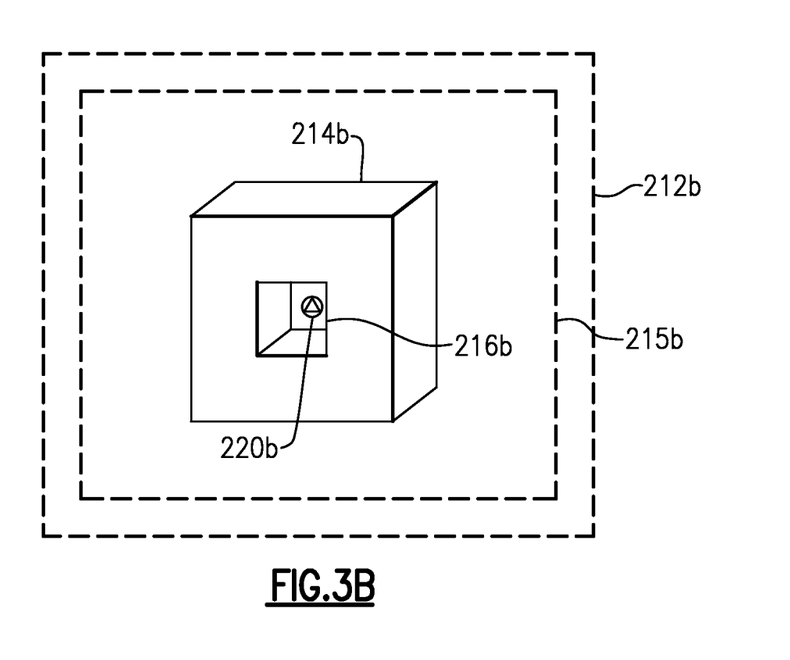
FIG. 3B illustrates a sample component of a part file displayed in a second CAx environment, according to an embodiment.

The exemplary components 214a, 214b interface with the post component 214a protruding through a through hole 216b. In alternative examples, any other type of interface can exist between the exemplary components 214a, 214b. Associated with the interface is at least one meta data file describing aspects of the interfacing that designers working on the components 214a, 214b need to know, but that are otherwise not included within the CAx environment.

In order to identify the presence of the meta data file within the part file stored in the database 109, an icon 220a, 220b is placed on a surface of the corresponding feature. The surfaces displaying the icon 220a, 220b are the features relevant to, or associated with, the meta data file. Further, to indicate that the surfaces are tied to the same meta data file, identical icons 220a, 220b are utilized in each of the components 214a, 214b. In alternative examples, the details of the icon, such as colour, shape, size etc. can be determined by the content of, or the type of, meta data file rather than utilized as a linking element to show a linkage between the two meta data files.

In some examples, the icons 220a, 220b further serve as a direct link to the meta data file, and allow a user in a given environment 212a, 212b to directly open the corresponding meta data file. By way of example, in some embodiments a user can click on the icon 220a, 220b and open the corresponding meta data file within the CAx environment 212a, 212b.

Further, because the meta data files are saved within the part file on the database 109 in the CAx system, each user independently has access to the meta data files any time they have access to the corresponding part file. If desired, this architecture may prevent linkage to meta data stored on a local computer hosting a user instance of the CAx environment 212a, 212b or stored at any other location that may not be accessible when that specific user is not participating in the CAx environment. In alternative embodiments, the meta data files can be simultaneously stored within the part file and in a distinct meta data file database In yet further alternative embodiments, the meta data file can be stored only in the distinct meta data file database, and an index file, or other similar file, can include a link from within the part database to the meta data file database.

In some examples, each local CAx environment 212a, 212b includes a meta data notification module that identifies the presence of meta data associated with a feature of a given component 214a, 214b, or associated with a given part file when a user enters the local CAx environment 212a, 212b. When meta data is identified by the meta data notification module, the meta data notification module provides a notice to the user that the meta data exists. In some examples, the meta data notification module is configured to cause a pop up window to appear within the viewing frustum 215a, 215b indicating that the component includes meta data associated with the part file. In other examples, the meta data notification module can highlight icons associated with the meta data file(s), cause the icons to flash, or utilize any other visual means of notifying the user that the component is associated with one or more meta data files.

Figure 4:
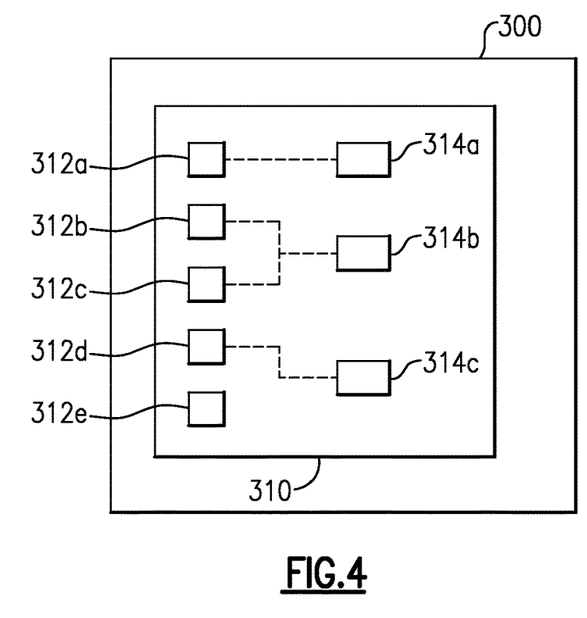
FIG. 4 illustrates a first exemplary database architecture.

In one embodiment of the above described meta data system, each meta data file is stored independently within the corresponding part file in the database. FIG. 4 illustrates an example architecture of a database 300 storing at least one part file 310, including multiple components 312a-e. Also stored within each part file 310 are meta data files 314a-c corresponding to that part file 310. In the illustrated example of FIG. 4, components 312*a* and 312*d* include corresponding meta files 314*a*, 314*c* that are linked to features of the corresponding components 312*a*, 312*d*. Components 312*b* and 312*c* are each linked to the same meta data file 314*b*. By way of example, multiple components 312*b*, 312*c* are linked to the same meta data file 314*b* when the meta data file 314*b* describes a shared feature of the components 312*b*, 312*c*, an interface between the components 312*b*, 312*c*, or similar features. A fifth component 312*e* within the part file 310 includes no linked meta data files.

While illustrated in the example of FIG. 4 as linking each component to a single meta data file, each component 312*a-e* could be linked to multiple distinct meta data files 314*a-c* within a given part file 310. By way of example, when a component 312*a-e* includes multiple features having corresponding meta data files 314*a-c*, each of the meta data files 314*a-c* is linked to the component file 312*a-c* within the part file 310.

Figure 5:
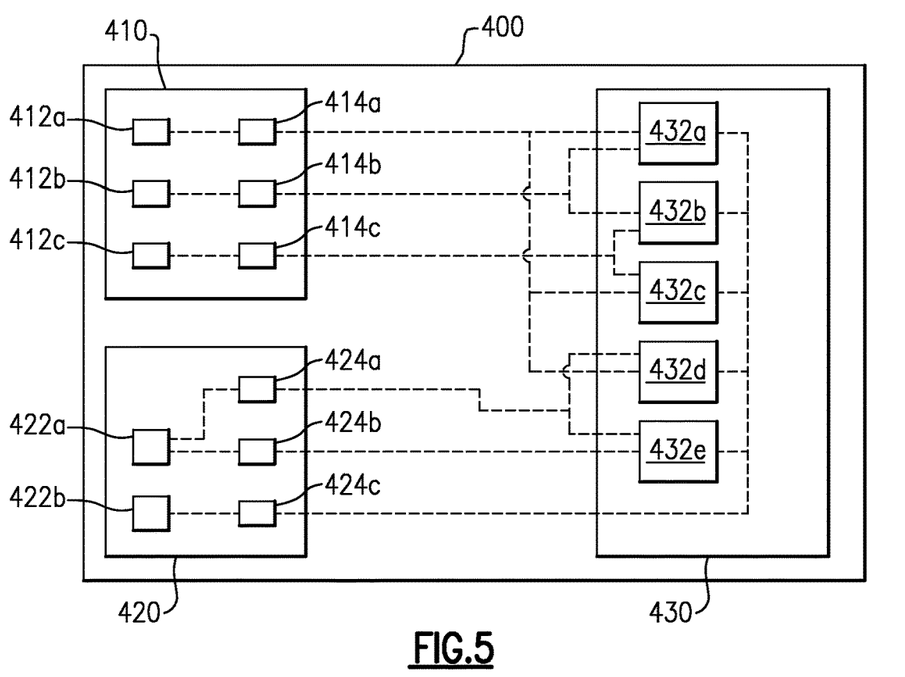
FIG. 5 illustrates a second exemplary database architecture.

In systems where multiple part files are stored within a single CAx database, and where multiple part files within the database re-use stock components or stock meta data files, an architecture such as the architecture illustrated in FIG. 4, where each meta data file is stored within each part file, can lead to multiple instances of the same meta data file being stored in a single database. This leads to excessive use of database memory, and can result in space constraints and/or operational delays in the multi-user CAx system. FIG. 5 illustrates an example architecture for a database 400 designed to minimize this type of excessive memory usage.

The exemplary database 400 of FIG. 5 includes two part files 410, 420 and a meta data database 430. Within each of the part files 410, 420 are multiple components 412*a-c*, 422*a-b*. Within the meta data database 430 are multiple meta data files 432*a-e*. Each component 412*a-c*, 422*a-b* includes one or more features associated with one or more of the meta data files 432*a-e*. Rather than each feature directly linking to the corresponding meta data file 432*a-e*, and storing the meta data files 432*a-e* in each part file 412*a-c*, 422*a-b*, each feature of a given component 412*a-c*, 422*a-b* that has one or more linked meta data files 432*a-e* is linked to a meta data index file 414*a-c*, 424*a-c*.

Each meta data index file 414*a-c*, 424*a-c* includes an additional link to one or more of the meta data files 432*a-e* within the meta data database 430. As can be seen in the illustrated example, each of the meta data files is linked to by multiple components 412*a-c*, 422*a-b*, without requiring the full meta data file 432*a-e* to be stored more than once within the database 400.

Further, as illustrated with the example component 422*a*, multiple features within a given component 412*a-c*, 422*a-b* can be linked to meta data files. In such a case, each feature is linked to a corresponding index file 424*a*, 424*b*, with the corresponding index files 424*a*, 424*b* being unique.

Referring again to FIGS. 3A and 3B, and with continued reference to the database architecture of FIG. 5, when a user in a CAx environment 212*a* opens the meta data corresponding to a given feature, the user is presented with the corresponding index file 414*a-c*, 424*a-c*. The index file 414*a-c*, 424*a-c* can then link to each of the corresponding meta data files, and include a header or description of the corresponding meta data files 432*a-e*, allowing the user to select only the meta data file containing information that the user wishes to view. In alternative examples, the action of selecting the icon 220, 220*b* can cause a meta data creation module within the CAx environment 212*a*, 212*b* to creat a temporary single meta data document including all of the meta data information linked to by the corresponding index file 414*a-c*, 424*a-c*.

With continued reference to FIGS. 1-5, FIG. 6 illustrates a flowchart showing an exemplary method for facilitating multi-user design in a CAx case.

Figure 6:
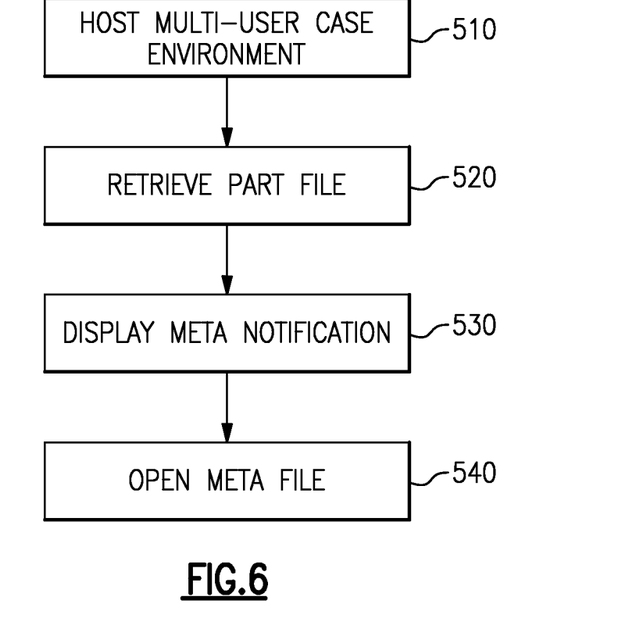
FIG. 6 illustrates an example method for facilitating multi-user design in a CAx system.

Initially, a host computer begins hosting a multi-user CAx environment at block 510. The host computer communicates with multiple local computers, each of which is operating a local CAx environment within the multi-user CAx environment.

Once the multi-user CAx environment has begun operating, the host computer retrieves a part file from a database at block 520. The part file is retrieved from a database configured to store multiple part files.

When the part file is retrieved, a meta notification is displayed by the host computer in each of the local CAx environments accessing a feature associated with the meta file at block 530. The notification is, in some examples, displaying an icon at or near the feature in a three dimensional view or a sketch view. The notification is, in other examples, a display of a string of characters within an attribute information view of a non-geometric feature.

In response to one or more of the users interacting with the displayed meta notification, the host computer will, in some examples, open the associated meta data file in one of the local CAx environments at block 540.

With continued reference to FIGS. 1-6, FIG. 7 illustrates an exemplary method for organizing a part database for a multi-user CAx system. Initially multiple part files are stored within a part file database in a multi-user CAx system at block 610. The system also stores at least one meta data file within the part database at block 620.

Figure 7:
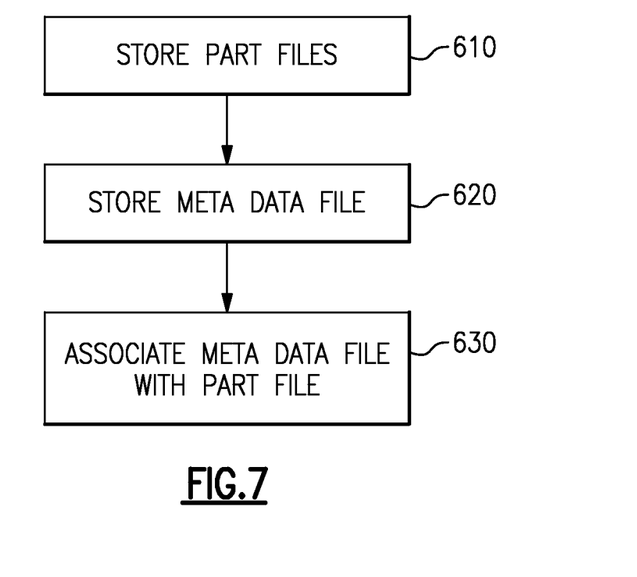
FIG. 7 illustrates an example method for organizing a part database for a multi-user CAx system.

The multi-user CAx further associates the meta data files with one or more features of a corresponding part file in the multiple stored part files at block 630. In some examples, the association is a direct link between the meta data file and the corresponding feature. In other examples, the association is achieved via an index file associated with the at least one feature and including one or more associated meta data files. In other examples, each meta data file is stored exactly once in the part database, and linked to multiple features.

Furthermore, the foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A system for executing software agnostic multi-user CAx environments comprising:
   a host computer including a processor and a memory, the processor and memory being configured to operate a multi-user CAx environment;
   said host computer configured to communicate with a plurality of local computers, each of said local computers including at least one CAx software package and being configured to operate a local CAx environment of said multi-user CAx environment;
   a part database configured to store a plurality of part files, each of said part files including at least one component having a plurality of features; and
   at least one meta data file stored within said part database, the meta data file being linked to at least two of said plurality of features via direct links, wherein the direct links are architectural connections between the meta data file and the at least two of said plurality of features.

2. The system of claim 1, wherein said at least one meta data file stored within said part database is linked to said at least one of said plurality of features via a meta data index file.

3. The system of claim 2, wherein each of said meta data index files is stored within a corresponding part file, and links to a corresponding meta data file stored within a meta data file database in said part database.

4. The system of claim 3, wherein said meta data file database is a distinct database from said part database.

5. The system of claim 2, wherein at least two of said plurality of features of said at least one component are linked to the same meta data file via distinct meta data index files.

6. The system of claim 2, wherein each unique meta data file is stored a single time within a meta data file database in said part file database.

7. The system of claim 1, wherein said multi-user CAx environment includes a meta data module configured to display one of an icon and a string characters in association with a feature, when said feature is displayed in said multi-user CAx environment.

8. The system of claim 7, wherein said multi-user CAx environment further includes a meta data notification module configured to notify a user of a presence of meta data files associated with a feature of a component displayed in said multi-user CAx environment.

9. The system of claim 1, wherein the at least one meta data file is at least one file having a file type outside of file types associated with the multi-user CAx system.

10. The system of claim 9, wherein said at least one meta data file is a file containing information related to a feature of a component to which said at least one meta data file is assigned, and wherein the information related to the feature is information that is outside the scope of the multi-user CAx system.

11. A method for facilitating multi-user design in a CAx system comprising:
hosting a multi-user CAx environment at a host computer including a processor and a memory;
said host computer communicating with a plurality of local computers, each of the local computers operating one of a plurality of local CAx environments within the multi-user CAx environment;
retrieving at least one part file having a plurality of features from a part database, the part database being configured to store multiple part files;
displaying a meta data notification in each of said local CAx environments accessing at least one of two features of said at least one part file, the features being associated with a meta data file in said part database, and the meta data notification being a feature of the at least one part file; and
opening said meta data file in one of said local CAx environments in response to a user in the local CAx environment interacting with said notification.

12. The method of claim 11, wherein displaying a meta data notification comprises displaying an icon at or near the feature in one of a three dimensional and a sketch view.

13. The method of claim 11, wherein displaying a meta data notification comprises displaying a string of characters in an attribute information view of a non-geometric feature.

14. A method for organizing a part database for a multi-user CAx system comprising:
storing a plurality of part files within a part database of a multi-user CAx system, wherein the multi-user CAx system includes a host computer including a processor and a memory, the processor and memory being configured to operate a multi-user CAx environment, and said host computer is configured to communicate with a plurality of local computers, each of said local computers including at least one CAx software package and being configured to operate a local CAx environment of said multi-user CAx environment;
storing at least one meta data file within said part database; and
associating the at least one meta data file in the part database with at least two features of a corresponding part file in said plurality of part files wherein said association between the at least one meta data file and the at least two features is a direct link, and the direct link is an architectural connection between the meta data file and the corresponding part file; and
wherein multiple features of the corresponding part file are associated with a single meta data file, and wherein each meta data file is stored exactly one time in said part database.

15. The method of claim 14, wherein said association between the at least one meta data file and the at least one feature is via an index file associated with the at least one feature.

* * * * *